(12) United States Patent
Zylber et al.

(10) Patent No.: US 8,603,146 B2
(45) Date of Patent: Dec. 10, 2013

(54) SYSTEM AND METHOD FOR INSERTION OF FLEXIBLE SPINAL STABILIZATION ELEMENT

(75) Inventors: Emmanuel Zylber, Marseilles (FR); Thomas Egli, Volketswil (CH); Nimrod Meier, Dachsen (CH); Michael Filippi, Schaffhausen (CH)

(73) Assignee: Zimmer GmbH, Winterthur (CH)

( * ) Notice: Subject to any disclaimer, the term of this patent is extended or adjusted under 35 U.S.C. 154(b) by 75 days.

(21) Appl. No.: 13/272,483

(22) Filed: Oct. 13, 2011

(65) Prior Publication Data

US 2012/0035664 A1 Feb. 9, 2012

Related U.S. Application Data

(63) Continuation of application No. 11/690,148, filed on Mar. 23, 2007, now Pat. No. 8,052,727.

(51) Int. Cl.
*A61B 17/70* (2006.01)

(52) U.S. Cl.
USPC .......................... 606/279; 606/86 A

(58) Field of Classification Search
USPC ................. 606/86 A, 86 R, 99, 103, 246–279
See application file for complete search history.

(56) References Cited

U.S. PATENT DOCUMENTS

| | | | |
|---|---|---|---|
| 2,267,925 A * | 12/1941 | Johnston ..................... | 606/66 |
| 5,540,688 A | 7/1996 | Navas | |
| 5,562,660 A | 10/1996 | Grob | |
| 6,290,700 B1 | 9/2001 | Schmotzer | |
| 6,986,771 B2 | 1/2006 | Paul et al. | |
| 6,989,011 B2 | 1/2006 | Paul et al. | |
| 7,008,424 B2 * | 3/2006 | Teitelbaum ..................... | 606/262 |
| 7,250,052 B2 | 7/2007 | Landry et al. | |
| 7,326,210 B2 | 2/2008 | Jahng et al. | |
| 7,744,629 B2 * | 6/2010 | Hestad et al. ................ | 606/246 |
| 2002/0035366 A1 * | 3/2002 | Walder et al. ................ | 606/61 |
| 2005/0010220 A1 * | 1/2005 | Casutt et al. ................ | 606/61 |
| 2005/0065516 A1 | 3/2005 | Jahng | |
| 2005/0085815 A1 | 4/2005 | Harms et al. | |
| 2005/0124991 A1 | 6/2005 | Jahng | |
| 2005/0143737 A1 | 6/2005 | Pafford et al. | |

(Continued)

FOREIGN PATENT DOCUMENTS

| EP | 669109 B1 | 5/1999 |
|---|---|---|
| EP | 1523949 B1 | 6/2007 |

(Continued)

*Primary Examiner* — Jan Christopher Merene
*Assistant Examiner* — Steven Cotroneo
(74) *Attorney, Agent, or Firm* — Seager, Tufte & Wickhem, LLC

(57) ABSTRACT

Insertion of a spinal stabilization element into a patient generally includes positioning a cord within a sheath and inserting the sheath and cord through the patient's body along a path generally toward an anchor member. An advancement member may be mounted on the leading end of the cord to further facilitate this insertion. The sheath is then retracted to expose a first portion of the cord within the patient's body, and the first portion of the cord is moved into a desired position relative to the anchor member. After advancing a spacer over the sheath and cord, the sheath is retracted to expose a second portion of the cord. The second portion of the cord is then moved into a desired position relative to another anchor member such that the spacer is positioned between the two anchor members.

15 Claims, 4 Drawing Sheets

(56) References Cited

U.S. PATENT DOCUMENTS

| | | |
|---|---|---|
| 2005/0154390 A1 | 7/2005 | Biedermann et al. |
| 2005/0203513 A1 | 9/2005 | Jahng et al. |
| 2005/0277922 A1* | 12/2005 | Trieu et al. .................. 606/61 |
| 2006/0111715 A1 | 5/2006 | Jackson |
| 2006/0142758 A1 | 6/2006 | Petit |
| 2006/0149242 A1* | 7/2006 | Kraus et al. .................. 606/61 |
| 2007/0005063 A1* | 1/2007 | Bruneau et al. .................. 606/61 |
| 2007/0016200 A1 | 1/2007 | Jackson |
| 2007/0055244 A1 | 3/2007 | Jackson |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |
| 2008/0147122 A1 | 6/2008 | Jackson |
| 2008/0177317 A1 | 7/2008 | Jackson |
| 2008/0183216 A1 | 7/2008 | Jackson |
| 2008/0234738 A1 | 9/2008 | Zylber et al. |
| 2008/0243188 A1* | 10/2008 | Walder et al. .................. 606/257 |
| 2009/0012563 A1* | 1/2009 | Alleyne et al. .................. 606/246 |

FOREIGN PATENT DOCUMENTS

| | | |
|---|---|---|
| FR | 2715057 B1 | 3/1996 |
| FR | 2844180 B1 | 8/2005 |
| FR | 2867057 B1 | 6/2007 |
| NL | 7610576 A | 3/1978 |
| WO | 9417745 A1 | 8/1994 |
| WO | 9519149 A1 | 7/1995 |
| WO | 9905980 A1 | 2/1999 |
| WO | 2004024011 A1 | 3/2004 |
| WO | 2005087121 A1 | 9/2005 |
| WO | 2006066685 A1 | 6/2006 |

* cited by examiner

SYSTEM AND METHOD FOR INSERTION OF FLEXIBLE SPINAL STABILIZATION ELEMENT

CROSS-REFERENCE TO RELATED APPLICATIONS

This application is a continuation of U.S. patent application Ser. No. 11/690,148, filed on Mar. 23, 2007, the entire disclosure of which is incorporated herein by reference.

FIELD OF THE INVENTION

This invention relates to surgical methods and associated installation systems for spinal stabilization, and more particularly to such systems and methods of inserting a flexible spinal stabilization element into a patient.

BACKGROUND

The spinal column is a highly complex system of bones and connective tissues that provides support for the body and protects the delicate spinal flexible connecting member and nerves. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal cord and nerves is located posterior to the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

One of the most common methods for treating spinal disorders is to immobilize a portion of the spine to allow treatment. Traditionally, immobilization has been accomplished by rigid stabilization. For example, in a conventional spinal fusion procedure, a rigid fixation rod is installed between pedicle screws secured to adjacent vertebrae. The fixation rod cooperates with the screws to immobilize the two vertebrae relative to each other so that fusion may occur. Fusion treatments using rigid stabilization, however, do have some disadvantages. For example, because the immobilized portion of the spine has reduced mobility, additional stresses are transferred to other portions of the spine neighboring or nearby the fused vertebrae. Fusion is also an irreversible procedure.

More recently, dynamic stabilization has been used in spinal treatment procedures. Dynamic stabilization does not result in complete spinal fusion, but instead permits enhanced mobility of the spine while also providing sufficient stabilization to effect treatment. One example of a dynamic stabilization system is the Dynesys® system available from Zimmer Spine, Inc. of Edina, Minn. Such dynamic stabilization systems typically include a flexible spacer positioned between pedicle screws installed in adjacent vertebrae of the spine. Once the spacer is positioned between the pedicle screws, a flexible cord is threaded through a channel in the spacer. The flexible cord is also secured to the pedicle screws by a retainer and set screw, thereby retaining the spacer between the pedicle screws while cooperating with the spacer to permit mobility of the spine.

The dynamic stabilization systems described above and others are naturally installed in a patient during a surgical procedure. Patient recovery from such surgical procedures is greatly enhanced if the tissue, muscle and other parts of the patient that are displaced and affected by the surgery are minimized, including the size and severity of the required incisions. For example, the cord can be inserted through a "puncture hole" or "access channel" used to implant one of the pedicle screws and then advanced to its installed position between the pedicle screws. Due to its flexible nature, however, the cord can be difficult to maneuver through the tissue. Additional tools are often required to accomplish this positioning. As a result, the access channels for the pedicle screws must be made large enough to accommodate the tools and any manipulation required. Increasing the size of the access channels increases the disruption of muscle tissue, which should be minimized to reduce scarring and promote faster recovery times. Therefore, systems and methods that further reduce the amount of disruption to the muscle tissue are highly desirable.

SUMMARY

This invention provides a system and method of inserting a flexible spinal stabilization element into a patient. The flexible spinal stabilization system generally includes an elongated flexible element, such as a cord, configured to be secured to first and second anchor members, such as pedicle screws, within the patient's body. The system also includes a spacer configured to be received over the flexible element. Those skilled in the art will appreciate, however, that other systems having similar components may be inserted into a patient according to the invention as well.

To insert the system, the flexible element is positioned within a sheath. The sheath may be formed from any suitable material for insertion into a patient's body. Advantageously, the sheath may be formed from a material having greater rigidity than the flexible element. The sheath and the flexible element are inserted into the patient's body at a first location on the patient's skin and along a path generally toward one of the anchor members. For example, the sheath and the flexible element may be inserted through the patient's skin at a location generally above the first anchor member and directed through the patient's body along a path extending toward the second anchor member. The shape of the sheath may help define the path, which may include a combination and straight and curved portions. The invention may also include a rigid advancement member mounted on the leading end of the flexible element for easier insertion, protection of the implant components, and other benefits described herein.

Once inserted or during the insertion, the sheath is retracted to expose a first portion of the flexible element within the patient's body. The first portion of the flexible element is then positioned in a desired position relative to the second anchor member. For example, the anchor member may be a pedicle screw having a retainer or head portion with a slot configured to receive the flexible element. In such an embodiment, the first portion of the flexible element may be positioned until it is properly located in the corresponding portion of the anchor member. A set screw or the like may be used to secure the first portion to the anchor member.

The system and method of inserting the stabilization system further comprises advancing a spacer over the sheath and the flexible element. After retracting the sheath to expose a second portion of the flexible element within the patient's body, the second portion of the flexible element is positioned relative to the first anchor member so that the spacer is positioned between the first and second anchor members. The second portion of the flexible element may be secured to the first anchor member similar to the way the first portion is secured to the second anchor member or in a different manner. Additionally, the flexible element may be cut proximate the second portion to define a separate segment.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

DETAILED DESCRIPTION

Figure 1:
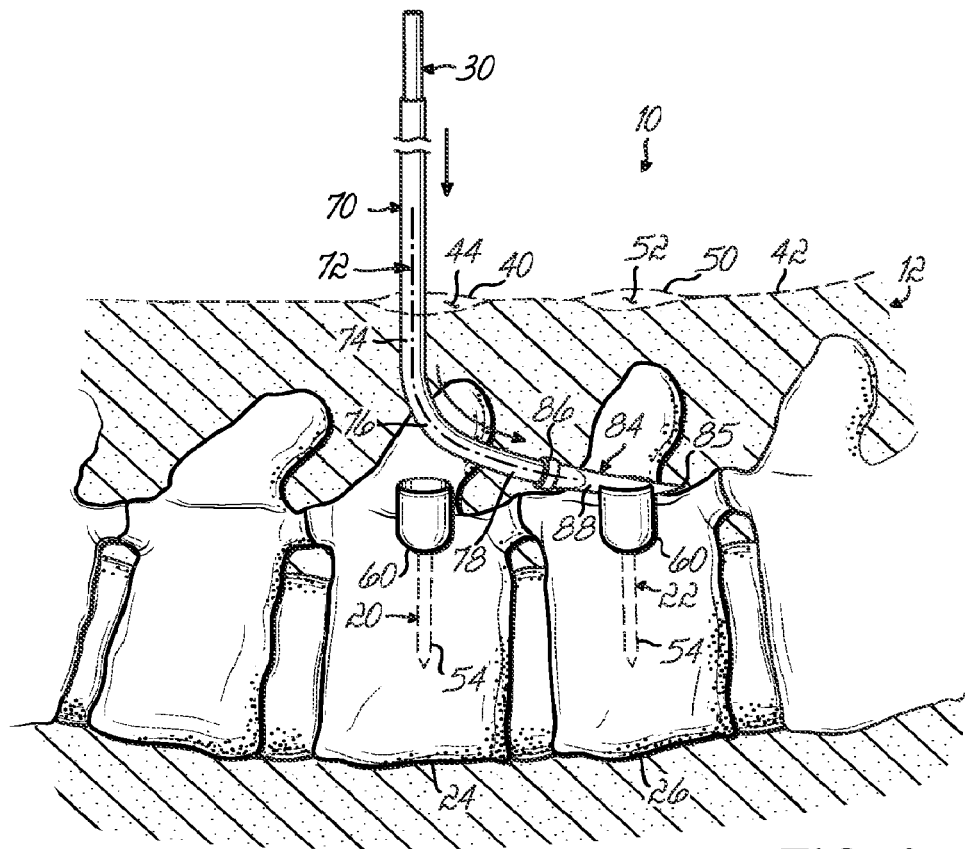
FIG. 1 is a schematic view showing a portion of a flexible spinal stabilization system being inserted into a patient according to various embodiments of this invention.

FIGS. 1-5 illustrate an exemplary embodiment of a dynamic spinal stabilization system 10 being inserted into the body 12 of a patient. The stabilization system 10 generally includes first and second anchor members 20, 22 secured to first and second vertebrae 24, 26 in the patient's body 12, a cord 30 configured to extend between the first and second anchor members 20, 22, and a spacer 32 configured to be received over the cord 30 between the first and second anchor members 24, 26. The cord may be formed, for example and without limitation, from polyethylene terephthalate (PET), titanium or metal materials, or other suitable materials recognized by those of skill in the art. The spacer 32 may be formed, for example and without limitation, from polycarbonate-urethane (PCU), polymeric and/or flexible materials, or other suitable materials recognized by those of skill in the art. In one embodiment, the stabilization system 10 is the Dynesys® system available from Zimmer Spine, Inc. of Edina, Minn. Those skilled in the art will appreciate, however, that the invention described below applies equally to other stabilization systems having similar components and/or operating upon similar principles.

Prior to inserting the stabilization system, the first and second anchor members 20, 22 are inserted into the patient's body 12. The first and second anchor members 20, 22 may be inserted using any technique known in the art. In one embodiment, a first incision 40 is made at a first location on the patient's skin 42 generally aligned above the first vertebra 24. The first anchor member 20 is inserted through the first incision 40 and advanced through the patient's body 12 so that it may be secured to the first vertebra 24. If desired, an access channel or puncture hole 44 may be established from the first incision 40 to the first vertebra 24 before inserting the first anchor member 20. The access channel 44 may be created by a needle or dilator (not shown) and optionally maintained by a cannula, retractor, or the like (not shown). Alternatively, the first anchor member 20 is driven through the body 12 after making the incision 40 to thereafter establish the access channel 44.

The second anchor member 22 may be inserted into the body 12 in a manner similar as the first anchor member 20. Specifically, a second incision 50 may be made at a second location on the patient's skin 42 generally aligned above the second vertebra 26. A second access channel 52 is established at the second incision 50, and the second anchor member 22 is advanced into the patient's body 12 so that it may be secured to the second vertebra 26. A wide variety of anchor members may be used with the stabilization system 10. The first and second anchor members 20, 22 shown in the drawings each include a pedicle screw 54 having a retainer member or housing 60 coupled to a top portion of the screw 54. As shown in FIG. 1A, each housing 60 includes a slot 62 configured to receive a portion of the cord 30. The housing 60 also includes internal threads 64 for receiving a set screw 66 (FIGS. 2-5), as will be described in greater detail below.

Prior to insertion, the cord 30 is positioned within a protective sheath 70. The sheath 70 may be made from any type of material suitable for insertion into a patient's body. In one embodiment, the sheath 70 is constructed from flexible polyethylene tubing having a rigidity greater than that of the cord 30. The strength of the sheath 70 and its ability to withstand compression forces enables it to be advanced through the tissue in the patient's body 12 without being significantly deflected. In other embodiments, the sheath can be constructed of materials such as metal to provide greater rigidity. Additionally, the cord 30 can be constructed from a flexible shape memory material such as nitinol. In its preferred configuration, the shape memory cord 30 can have a straight configuration. After loading the cord 30 into the sheath 70 or surrounding it with the sheath 70, the shape memory cord 30 can take on or conform to the configuration of the sheath 70. For example, the shape memory cord 30 can go from straight to curved. After receiving the sheath 70, the shape memory cord 30 can return to its preferred straight configuration within the housing 60 of an anchor member 20, 22.

Additionally, an advancement member 84 may be mounted on a leading end 34 of the cord 30 and in advance of the sheath 70. The advancement member 84 may be metal or any other type of material suitable for insertion into the patient's body 12. The advancement member 84 may include a leading tip 85 to facilitate movement of the cord 30 and/or sheath 70 through tissue, a main body portion 88, and a receiver section 86 adapted to accept the leading end 34 of the cord 30 and/or the leading end of the protective sheath 70. Furthermore, the advancement member 84 may have any configuration, including a bent or curved profile, to assist the surgeon when inserting the advancement member 84, cord 30, and sheath 70 into the patient. The advancement member 84 offers the advantages of easier insertion of the cord 30 into the patient, may provide fluoroscopy marking, and protects the cord 30 or other implant during manipulation by the surgeon with clamps or other instruments. The tip 85 can have any configuration such as a needle, bullet nose, or tapered shape to facilitate movement through tissue.

Figure 1A:
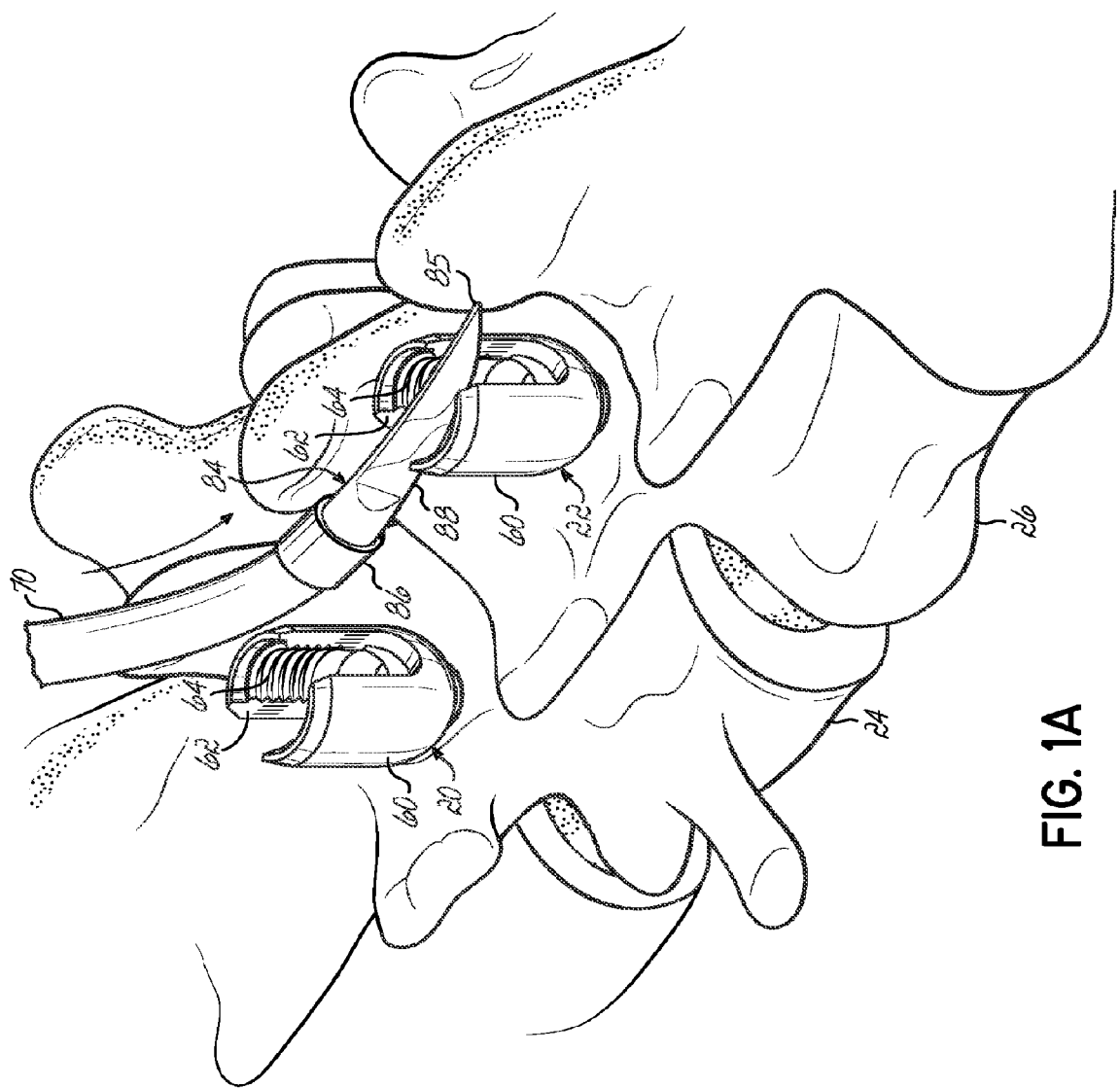
FIG. 1A is a perspective view of the portion of the flexible spinal stabilization system illustrated in FIG. 1.

Therefore, as shown in FIG. 1, the advancement member 84, sheath 70, and cord 30 are inserted through the first incision 40 and along a path 72 through the patient's body 12 generally toward the second anchor member 22. The cord 30 may be positioned within the sheath 70 and advancement member 84 such that no portion of the cord 30 is directly exposed to the patient's body 12 during this insertion. Alternatively, the end 34 of the cord 30 may extend slightly beyond the sheath 70, but not far enough to significantly affect the insertion of the sheath 70 and the cord 30. The path 72 along which the advancement member 84, cord 30, and sheath 70 are inserted may include a combination of generally straight sections and curved sections. For example, in one embodiment, the path 72 includes a first generally straight section 74, an intermediate curved section 76, and a second generally straight section 78. Such an arrangement allows the sheath 70 and the cord 30 to be "fished" downwardly for a distance before being directed transversely toward the second anchor member 22.

At some point after or during the insertion, the advancement member 84 is removed through the incision 50 and the sheath 70 is retracted to expose a first portion 80 of the cord 30 within the patient's body 12. Alternatively, the cord 30 can be affixed to the advancement member 84 and the cord 30 is pulled up through the incision 50. The excess portion of the cord 30 can then be cut off the flexible construct.

Figure 2:
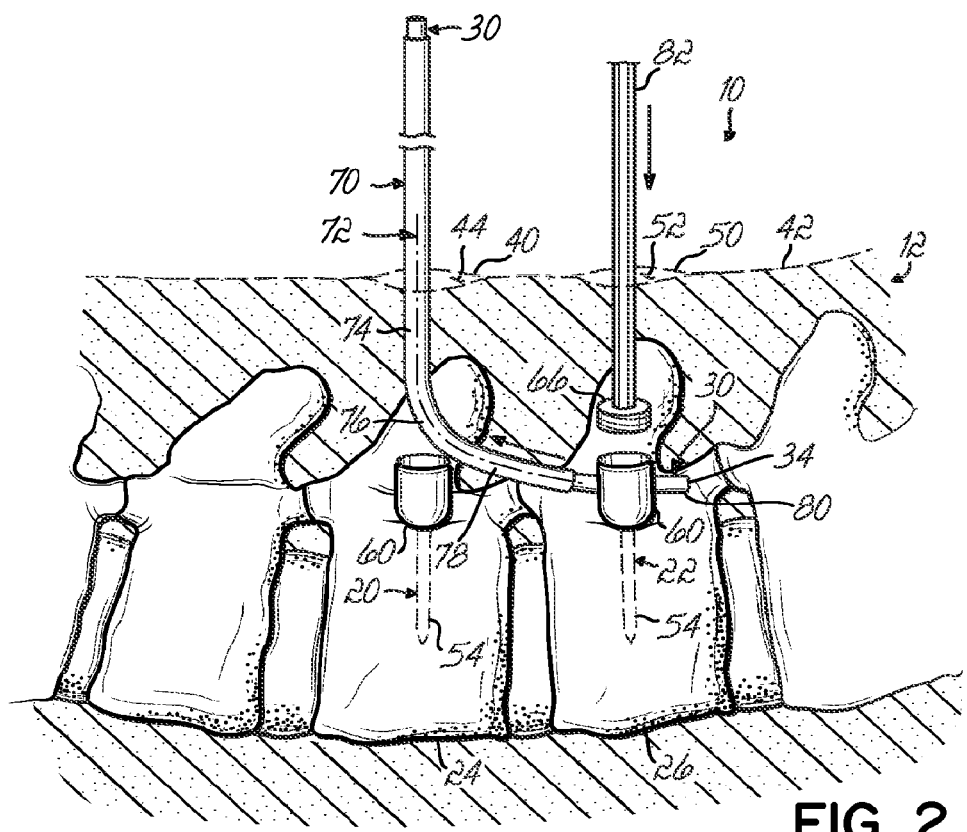
FIGS. 2-5 are schematic views sequentially illustrating the flexible spinal stabilization system of FIG. 1 being further inserted into the patient.

The first portion 80 of the cord 80 is proximate the end 34. As shown in FIG. 2, the first portion 80 is moved into a desired position relative to the second anchor member 22. This may involve positioning the first portion 80 of the cord 30 in the slot 62 of the associated housing 60. A positioning tool 82 may be inserted through the second access channel 52 to push the first portion 80 of the cord 30 into the slot 62. The positioning tool 82 may be the same or a different tool than that used to deliver a set screw 66 to the second anchor member 22.

Figure 3:
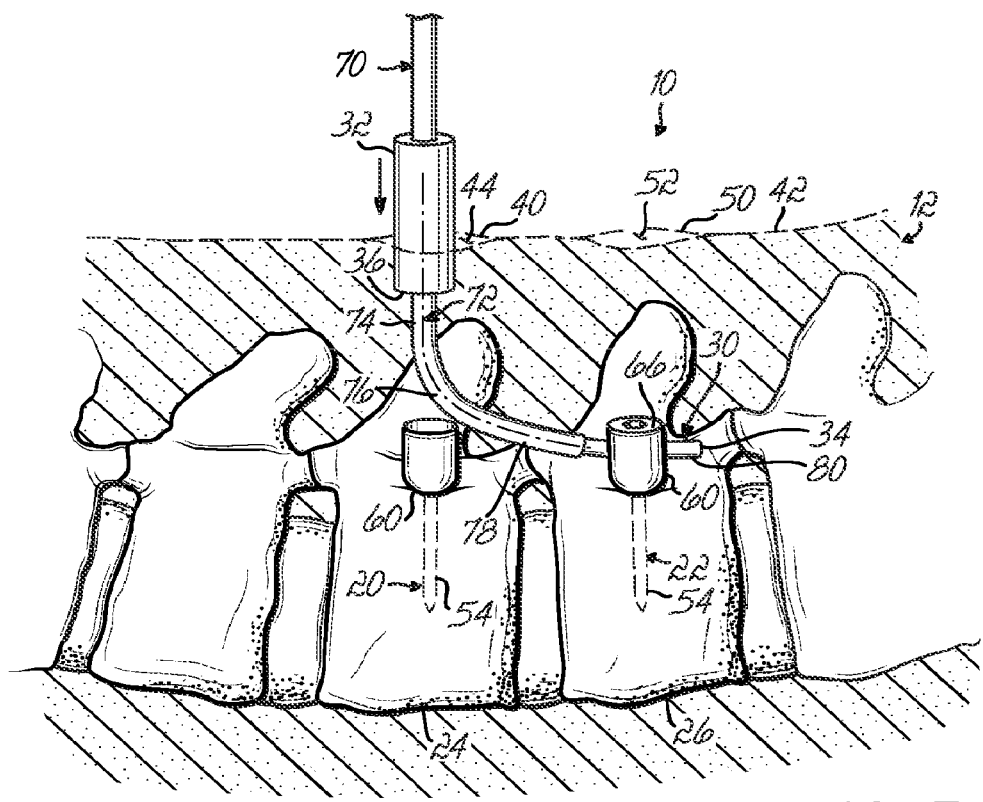

FIG. 3 illustrates the system 10 after the first portion 80 of the cord 30 is secured to the second anchor member 22. Specifically, the set screw 66 has been inserted through the second access channel 52 and into the housing 60 of the second anchor member 22. External threads (not shown) on the set screw 66 engage the internal threads 64 (FIG. 1A) of the housing 60 to secure the components. The set screw 66 cooperates with the housing 60 to secure the first portion 80 so that the cord 30 cannot be easily pulled away from the second anchor member 22. Although only the set screw 66 is shown, a wide variety of other devices or fastening elements may be used to secure the first portion 80 instead of or in addition to the set screw 66. For example, the second anchor member 22 may alternatively include a portion adapted to cooperate with a cap (not shown) for retaining the first portion 80 of the cord 30.

Figure 4:
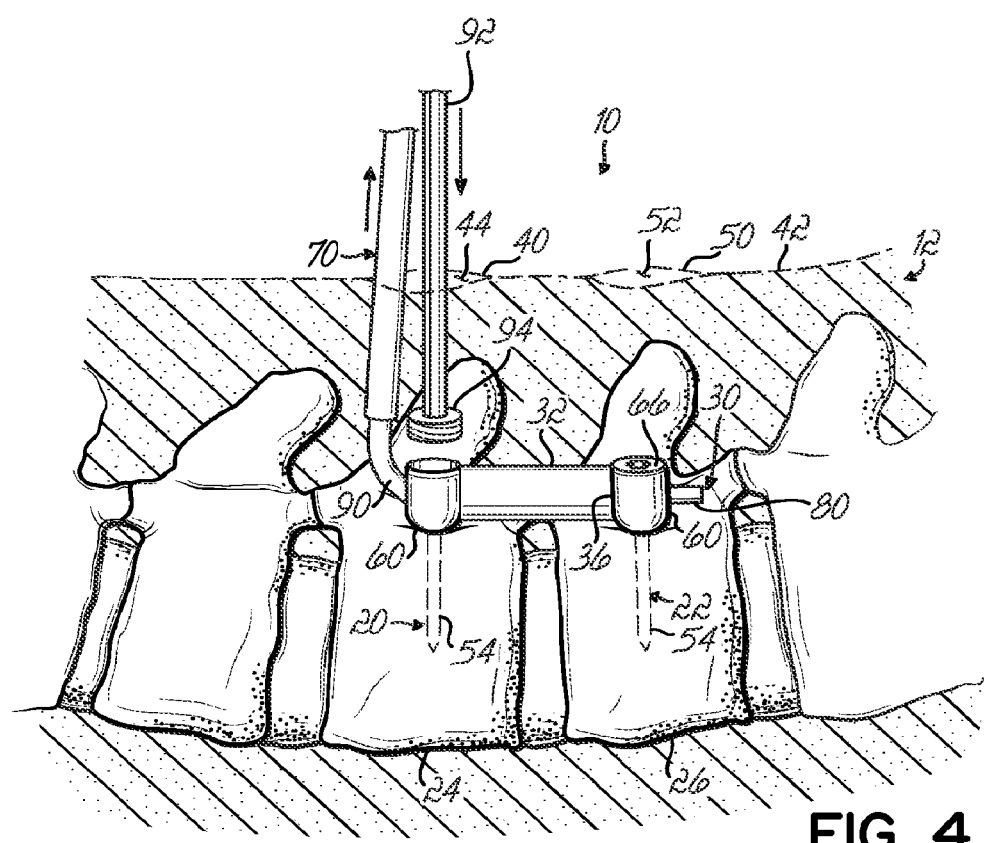

Still referring to FIG. 3, the spacer 32 is advanced over the sheath 70 and the cord 30 into the patient's body 12. Alternatively, the sheath 70 can be removed and the spacer 32 placed directly over the cord 30. The spacer 32 is advanced until a first end 36 is positioned proximate the second anchor member 22. For example, the spacer 32 may be advanced until the first end 36 abuts the retainer element 60 of the second anchor member 22. As shown in FIG. 4, the sheath 70 is further refracted to expose a second portion 90 of the cord 70, which is moved into a desired positioned relative to the first anchor member 20 so that the spacer 32 extends between the first and second anchor members 20, 22. The sheath 70 may be retracted before or during the positioning of the second portion 90. Additionally, as with the first portion 80, a positioning tool 92 may be inserted through the first access channel 44 to push the second portion 90 into the slot 62 of the housing 60. A set screw 94 or other device is used to secure the second portion 90 within the housing 60.

Figure 5:
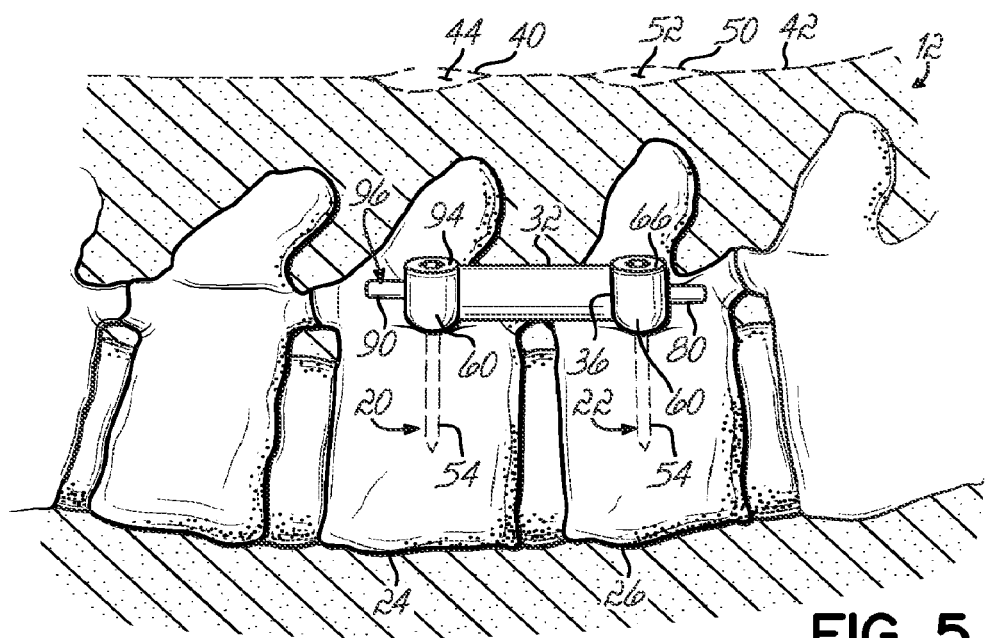

FIG. 5 illustrates a cord segment 96 formed after cutting the cord 30 proximate the second portion 90. The cord segment 96 includes the first and second portions 80, 90 and extends between the first and second anchor members 20, 22. The remainder of the cord 30 (not shown) from which the segment 96 was cut has been removed from the patient's body 12 through the first incision 40.

As a result of the above-described insertion procedure, the need to create incisions or access channels large enough to accommodate tools for maneuvering the cord 30 through tissue is reduced or eliminated. The advancement member 84 and/or protective sheath 70 are able to guide the cord through tissue along a desired path. To this end, the invention takes advantage of the incisions already made to insert the first and second anchor members 20, 22, thereby reducing or minimizing any additional disruption of tissue required to complete the surgical procedure. If desired, however, the cord 30 may be inserted through an incision or access channel different than those used to implant the first and second anchor members 20, 22. Use of the advancement member 84 and/or protective sheath 70 also allow for aseptic handling of the cord 30 prior to its final placement within the patient's body 12. Such handling helps reduce the risk of deep wound infections.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, the invention described above may be used to position the cord 30 between more than two anchor members or more than two vertebrae. To this end, the cord 30 may be positioned between first, second, and third anchor members secured to respective first, second, and third vertebrae. Additionally, the sheath 70 and cord 30 may be inserted into the patient's body 12 with the first portion 80 already partially or fully exposed. Moreover, the sheath is shown and described in one embodiment as being a tubular member, but the sheath may be of another configuration that may or may not entirely surround the cord, a helical element or some other structure extending over a length of the cord and providing added rigidity to the cord during installation. The sheath may include multiple component parts assembled together from the same or variety of different materials.

The invention in its broader aspects is therefore not limited to the specific details, representative apparatus and methods and illustrative examples shown and described. Accordingly, departures may be made from such details without departing from the scope or spirit of the inventor's general inventive concept.

What is claimed:

1. A method of inserting a spinal stabilization system into a patient, the method comprising:
    engaging a first anchor member to a first vertebra, the first anchor member including a housing having an open slot defined between opposing legs of the housing;
    engaging a second anchor member to a second vertebra, the second anchor member including a housing having an open slot defined between opposing legs of the housing;
    inserting a flexible element positioned within a sheath through a first incision at a first location on the patient's skin and along a path through the patient's body generally toward the second anchor member;
    moving an exposed first portion of the flexible element extending beyond a distal end of the sheath into the slot of the second anchor member and then securing the exposed first portion in the slot of the second anchor member;
    advancing a spacer over the flexible element such that the spacer is positioned between the first and second anchor members after the first portion of the flexible element is secured in the slot of the second anchor member;

retracting the sheath proximally relative to the flexible element to expose a second portion of the flexible element after the first portion of the flexible element is secured in the slot of the second anchor member; and after advancing the spacer over the flexible element to a position between the first and second anchor members, moving the exposed second portion of the flexible element into the slot of the first anchor member and then securing the exposed second portion in the slot of the first anchor member.

2. The method of claim 1, wherein the flexible element is within the sheath during advancement of the spacer over the flexible element.

3. The method of claim 1, further comprising:
cutting the flexible element proximate the second portion.

4. The method of claim 1, wherein the inserting the flexible element through the first incision and along the path step further comprises:
simultaneously directing the sheath and the flexible element downwardly along a first generally straight section of the path, through a curved section of the path, and toward the second anchor member along a second generally straight section of the path.

5. The method of claim 1, further comprising:
inserting a positioning tool through a second incision at a second location on the patient's skin and through the patient's body to push the exposed first portion of the flexible element into the slot of the second anchor member.

6. The method of claim 1, wherein the exposed first portion of the flexible element is secured in the slot of the second anchor member with a set screw.

7. The method of claim 1, further comprising:
inserting a positioning tool through the first incision and into the patient's body to push the exposed second portion of the flexible element into the slot of the first anchor member.

8. The method of claim 1, wherein the exposed second portion of the flexible element is secured in the slot of the first anchor member with a set screw.

9. The method of claim 1, wherein the distal end of the sheath is positioned between the first and second anchor members while the spacer is advanced over the flexible element.

10. A method of inserting a spinal stabilization system into a patient, the method comprising:
engaging a first anchor member to a first vertebra, the first anchor member including a housing having an open slot defined between opposing legs of the housing;

engaging a second anchor member to a second vertebra, the second anchor member including a housing having an open slot defined between opposing legs of the housing;

inserting a flexible element positioned within a sheath through a first incision at a first location on the patient's skin and along a path through the patient's body generally toward the second anchor member;

moving an exposed first portion of the flexible element extending beyond a distal end of the sheath into the slot of the second anchor member and then securing the exposed first portion in the slot of the second anchor member;

advancing a spacer over the flexible element such that the spacer is positioned between the first and second anchor members after the first portion of the flexible element is secured in the slot of the second anchor member;

retracting the sheath proximally relative to the flexible element to expose a second portion of the flexible element after the first portion of the flexible element is secured in the slot of the second anchor member; and after advancing the spacer over the flexible element to a position between the first and second anchor members, moving the exposed second portion of the flexible element into the slot of the first anchor member and then securing the exposed second portion in the slot of the first anchor member;

wherein the flexible element includes an advancement member mounted on a leading end of the flexible element and extending beyond the distal end of the sheath.

11. The method of claim 10, wherein the advancement member includes a receiver section configured to receive the distal end of the sheath.

12. The method of claim 11, wherein the advancement member, the flexible element and the sheath are simultaneously directed through the first incision and along the path through the patient's body generally toward the second anchor member.

13. The method of claim 10, further comprising:
removing the advancement member from the flexible element after securing the exposed first portion of the flexible element in the slot of the second anchor member.

14. The method of claim 13, further comprising:
removing the advancement member from the patient's body through a second location on the patient's skin.

15. The method of claim 13, wherein the advancement member is removed from the flexible element by cutting the flexible element between the housing of the second anchor member and the advancement member.

* * * * *

UNITED STATES PATENT AND TRADEMARK OFFICE
CERTIFICATE OF CORRECTION

| | |
|---|---|
| PATENT NO. | : 8,603,146 B2 |
| APPLICATION NO. | : 13/272483 |
| DATED | : December 10, 2013 |
| INVENTOR(S) | : Emmanual Zylber et al. |

Page 1 of 1

It is certified that error appears in the above-identified patent and that said Letters Patent is hereby corrected as shown below:

In the Specification

Column 5, Line 55: delete "refracted" and insert -- retracted --.

Signed and Sealed this
Twenty-fifth Day of February, 2014

Michelle K. Lee
*Deputy Director of the United States Patent and Trademark Office*